United States Patent [19]

Miller et al.

[11] 4,124,558

[45] Nov. 7, 1978

[54] ALKYL 9,9(10,10)-BIS(ACYLOXYMETHYL)OCTADECANOATES AS PRIMARY PLASTICIZERS FOR POLYVINYLCHLORIDE

[75] Inventors: William R. Miller; Everett H. Pryde, both of Peoria, Ill.

[73] Assignee: The United States of America as represented by the Secretary of Agriculture, Washington, D.C.

[21] Appl. No.: 884,323

[22] Filed: Mar. 7, 1978

Related U.S. Application Data

[62] Division of Ser. No. 764,113, Jan. 31, 1977, Pat. No. 4,093,637.

[51] Int. Cl.$^2$ .......................... B01F 9/00; B01F 15/02
[52] U.S. Cl. ............................. 260/31.6; 260/23 XA; 260/410.9 R; 260/413
[58] Field of Search .......... 260/23 XA, 31.6, 410.9 R, 260/410.9 Q, 413 R, 413 Q

[56] References Cited

U.S. PATENT DOCUMENTS 4,083,816   6/1976   Frankel et al. ...................... 260/31.2

OTHER PUBLICATIONS

Frankel et al., Jour. Am. Oil Chemist. Soc., vol. 52, No. 12, pp. 498–504 (1975).
Frankel et al., IJEC Pd. Research and Development, vol. 12, p. 47, Mar. 1973.

*Primary Examiner*—John Niebling
*Attorney, Agent, or Firm*—M. Howard Silverstein; David G. McConnell; Curtis P. Ribando

[57] ABSTRACT

Alkyl 9,9(10,10)-bis(acyloxymethyl)octadecanoates were prepared from 9(10)-formylstearic acid and found to function as primary plasticizers. Polyvinylchloride resins plasticized by these compounds have permanence and heat stability properties superior to those of resins plasticized with dioctyl phthalate, dioctyl sebacate, or other commercially available plasticizers.

13 Claims, No Drawings

ALKYL 9,9(10,10)-BIS(ACYLOXYMETHYL)OCTADECANOATES AS PRIMARY PLASTICIZERS FOR POLYVINYLCHLORIDE

This is a division, of application Ser. No. 764,113, filed Jan. 31, 1977 now U.S. Pat. No. 4,093,637.

BACKGROUND OF THE INVENTION

1. Field of the Invention

This invention relates to the preparation of novel geminal hydroxymethyl compounds from 9(10)-formylstearic acid and also the acyloxy derivatives of such compounds useful as primary plasticizers for polyvinylchloride (PVC).

2. Description of the Prior Art

A plasticizer is a material which is incorporated in a plastic and which functions to increase its workability and flexibility. The search for acceptable plasticizers has been a very active one. In 1934 about 56 plasticizers were being produced and from that time until about 1943, over 20,000 plasticizer compositions had been disclosed in the literature, 60 of which are among the 500 presently available (cf. *Encyclopedia of Polymer Science and Technology*, Vol. 10, John Wiley and Sons, Inc., 1969, p. 230).

Primary plasticizers are plasticizers which are miscible with the polymer in amounts sufficient to impart the desired characteristics to the final product without exuding. Secondary plasticizers are those which are not soluble in the polymer in the desired amounts and, therefore, must be used in smaller amounts in combination with another more compatible plasticizer. "Compatibility" is the term used to describe the ability of two or more substances to mix with each other to form a homogenous mixture. The desired plastic product is formed by vigorously mixing polymer and plasticizer at elevated temperature (about 160° C. for polyvinylchloride) until "fusion" takes place. Fusion is the mechanism by which plasticizer and polymer become a homogenous mixture and, therefore, the ease of fusion is directly related to compatibility.

It is generally believed that in PVC, ease of fusion tends to decrease with increasing molecular size and decreasing polarity, and that addition of a carbon atom linkage to the plasticizer molecule causes a reduction in its compatibility for PVC (*Encyclopedia of Polymer Science and Technology*, supra, p. 250). Moreover, it would be expected that the addition of several carbon atoms would reduce compatibility even further.

The types of organic plasticizers in general use are liquids having moderately high molecular weights and include esters of carboxylic acids, esters of phosphoric acids, hydrocarbons, halogenated hydrocarbons, ethers, polyglycols, and sulfonamides. For reasons of compatibility, costs, process behavior, and performance, primary PVC plasticizers are generally limited to various dibasic acid and phosphate esters, epoxidized oils and resins, glycolates, mellitates, and polyesters of various dibasic acids with glycols, pentaerythritol derivatives, and sulfonates. Secondary PVC plasticizers are generally limited to various aromatic and mixed aromatic aliphatic oils, chlorinated paraffins, polyalpha-methyl styrene derivatives and esters of high molecular weight alcohols and organic acids (cf. *Modern Plastics Encyclopedia*, Vol. 50, No. 1A, 1973-74, pp. 254-266).

Dioctyl phthalate (DOP) is the most widely used primary plasticizer for polyvinylchloride and accounts for about 25% of the total market (*Encyclopedia of Polymer Science and Technology*, supra, p. 231). However, because of its volatility, migration, and incomplete biodegradability, DOP is suspect as a ubiquitous environmental contaminant. Other commercial plasticizers such as diocty sebacate (DOS) and dioctyl azelate (DOZ) suffer from high percent migration loss and poor compatibility with PVC. Any new plasticizer to be superior to DOP would have to show lower volatility, migration, and solvent extractability, as well as better biodegradability.

Efforts to fine a substitute for DOP as a primary plasticizer have led to the investigation of derivatives of $C_{18}$ unsaturated fatty acids.

Gruber et al., U.S. Pat. No. 2,332,849, teaches oxidizing and esterifying oleic acid to trans-9,10-dihydroxystearic acid methyl ester, which is then reacted with acetic anhydride to yield trans-9,10-diacetoxy stearic acid methyl ester.

Knight et al., J. Amer. Oil Chem. Soc. 36: 382-388 (Sept. 1959), reports on a number of acyloxy and aryloxy compounds prepared from hydroxystearic acids.

Birum et al., U.S. Pat. No. 2,965,598, oxidizes the oxonation products of oleic acid and oleic acid esters and subsequently esterifies the resultant acids with a series of alcohols. The resultant esters have some utility as plasticizers.

Wheeler et al., U.S. Pat. No. 3,016,359, prepares plasticizers by an oxonation reaction similar to that of Birum et al., supra, and further teaches other $C_{18}$ unsaturated acids as the starting material. Specifically taught are linoleic, linolenic, ricinoleic, and elaidic acids.

Bhatnagar et al., Ind. Chem. J., Ann., pp. 136-137 (1972), produces primary plasticizers by epoxidization of acetylated castor oil and by the acetylation of ricinoleates of glycerol.

Awl et al. [U.S. Pat. No. 3,983,067; J. Amer. Oil Chem. Soc. 49(4): 222-228 (1972); and J. Amer. Oil Chem. Soc. 51(5): 224-228 (1974)] reports on the plasticizing properties of ethylene acetals and dimethyl acetals from hydroformylated polyunsaturated vegetable oils and esters.

Frankel et al., J. Amer. Oil Chem. Soc. 52(12): 498-504 (1975), reports on a number of acyl esters from oxo-derived hydroxymethyl-stearates and compares them to various commercial plasticizers.

All of the prior art compounds discussed above exhibited some plasticizing properties. However, it has generally been observed that none of the heretofore known unsaturated fatty compound oxo-derivatives are significantly superior to DOP to successfully replace it as the leading plasticizer for PVC where improved permanence is desired. The primary problem in the art exists in combining good thermal stability and low migration and volatility with satisfactory compatibility.

SUMMARY OF THE INVENTION

The object of this invention is the provision of compositions which are useful as primary plasticizers for PVC, which are easily prepared from inexpensive starting materials, particularly 9(10)-formylstearic acid and its alkyl esters, and which impart to the PVC permanence and heat stability properties superior to those of PVC compositions plasticized with commercially available plasticizers such as DOP. Incidental with the fulfillment of this objective is the development of a biodegradable substitute for nonrenewable resource-derived plasticizers, and the elimination of DOP as an environmental contaminant.

In accordance with the above objects, we have found a method of preparing the novel primary plasticizers for PVC via a novel intermediate compound according to the following sequence of steps:

(1) converting 9(10)-formylstearic acid or an alkyl ester thereof to the novel intermediate compound 9,9(10,10)-bis(hydroxymethyl)octadecanoic acid by means of the Tollens condensation and crossed Cannizzaro reactions;

(2) esterifying the acid from step (1) with a $C_1$-$C_8$ straight or branched alkyl alcohol;

(3) acylating the ester from step (2) to yield the novel primary plasticizers having the general structure:

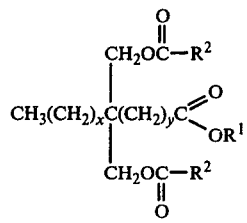

where
$R^1$ = $C_1$-$C_8$ straight or branched alkyl;
$R^2$ = $C_1$-$C_4$ straight or branched alkyl or halogen-substituted alkyl;
$x$ = 7 or 8; and
$y$ = 7 or 8 with the proviso that
$x + y$ = 15; and (4) recovering the primary plasticizers prepared in step (3).

The compositions thus prepared in step (3) are then fused in plasticizers amounts with PVC.

DESCRIPTION OF THE PREFERRED EMBODIMENTS

The basis starting material for use in the instant invention is selected from 9(10)-formylstearic acid (FSA) or one of its lower alkyl ($C_1$-$C_4$) esters; namely, alkyl 9(10)-formylstearate (AFS). FSA and AFS are conveniently obtained by the selective hydroformylation of oleic acid or its alkyl esters, respectively, as taught by E. N. Frankel, J. Amer. Oil Chem. Soc. 48(5): 248–253 (1971). The hydroformylation reaction disclosed therein yields approximately an equal mixture of 9- and 10-formylated products. Of course, it is understood that FSA and AFS from other sources would be operable in the invention.

The first step in the preparation of the instant plasticizers involves converting the FSA or AFS to the novel compound 9,9(10,10)-bis(hydroxymethyl)octadecanoic acid [bis(hydroxymethyl) stearic acid], hereafter referred to as BHMOA. The reaction of formaldehyde with aliphatic aldehydes to form (hydroxymethyl)aldehydes is the well-known Tollens condensation as described by A. T. Nielsen and W. J. Houlihan in Org. React. 16: 15 (1968). By virtue of this condensation, all hydrogens alpha to the aldehyde function are replaced by hydroxymethyl groups. The aldehyde function is then reduced to an alcohol by a crossed Cannizzaro reaction as reported by T. A. Geissman, Org. React. 2: 99 (1944). This process is used commercially for the production of pentaerythritol (J. F. Walker in *The Encyclopedia of Chemistry*, Third Edition, C. A. Hampel and G. G. Hawley, eds., VanNostrand Reinhold Co., New York, New York, 1973, p. 43), and also for the conversion of hexanol and nonanal to their respective triols as taught by D. J. Moore and E. H. Pryde, J. Amer. Oil Chem. Soc. 45: 517 (1968). In the instant process, the crossed Cannizzaro reaction proceeds spontaneously under the conditions of the Tollens condensation without the need to isolate the hydroxymethyl aldehyde. This reaction is outlined as follows:

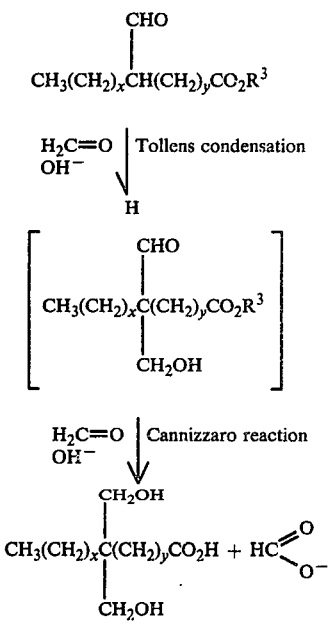

9,9(10,10)-bis(hydroxymethyl)octadecanoic acid (BHMOA)
where
$R^3$ = H or $C_1$-$C_8$ straight or branched alkyl;
$x$ = 7 or 8; and
$y$ = 7 or 8 with the proviso that $x + y$ = 15.

Though the above reaction combination is well known as applied to short-chain aldehydes, supra, it was uncertain that it would be operable when applied to any of the long-chained and sterically-hindered FSA or AFS. It was particularly unexpected that BHMOA would be obtained in near-quantitative yield. The reaction conditions for preparing BHMOA are the same as those which are well known in the art for converting short-chain aldehydes as per Walker and Moore et al., supra, and are further exemplified in Examples 1–3 below. It is noted in Example 1 that the FSA can be dissolved in methanol, and the formaldehyde solution contains sufficient sodium hydroxide to neutralize the FSA as well as the formic acid formed by the Cannizzaro reaction. Alternatively, Example 2 shows that the FSA may be dissolved in a sodium hydroxide solution which contains only slightly more than the equivalent amount of base required to dissolve the acid. When an AFS is used as the starting material as in Example 3, it is saponified by the added base before the reaction proceeds.

BHMOA is recovered from the reaction mixture as an extremely viscous liquid which is difficult to purify by conventional means. In the commercial production of the instant plasticizers, it may be desirable to omit purification. However, it was unexpectedly discovered that the acetals of alkyl esters of BHMOA can be readily prepared and that these relatively volatile compounds can be easily purified by fractional distillation. These compounds could then be used in the preparation of the instant plasticizers. The acetone acetal methyl ester is the preferred derivative for purposes of fractional distillation in view of its distillability and the availability of the reagents used in its preparation. This derivative will therefore be used in the ensuing description for purposes of illustration only, with the understanding that other acetals prepared from other suitable ketones, aldehydes, or acetalating agents and their alkyl esters, particularly $C_1$–$C_8$ straight or branched, could be substituted as equivalents therefor.

In a step-by-step procedure, the methyl ester of BHMOA is prepared by reacting BHMOA with methanol under acid conditions as would be within the ordinary skill of a person in the art. The ester is then reacted with acetone in the presence of an acid catalyst to yield the acetone acetal. Though any known acid catalyst would be operable, p-toluenesulfonic acid is preferred. The addition of a small amount of 2,2-dimethoxypropane (DMP) may also be added to ensure complete acetalation. The steps of acetalation and esterification may also be reversed, though at the expense of deacetalation of a minor proportion of material during the esterification step. The preferred method of preparing the acetal ester is to conduct both reactions simultaneously by reaction of the BHMOA with methanol and DMP in the presence of the acid catalyst as outlined below:

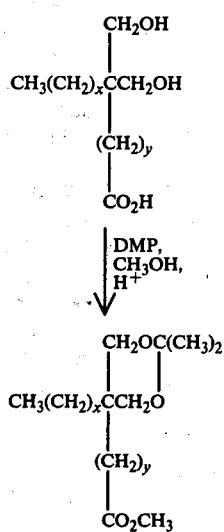

As illustrated in Example 4–9, the acetalation may be conducted at room temperature and the esterification at reflux. Quantities of alcohol and DMP in excess of the stoichiometric amounts required by the reaction are used. Recovery of the purified acetal-ester can be accomplished by conventional means, such as vacuum distillation. Alternatively, the crude ester-acetal may be extracted with base before distillation in order to remove residual BHMOA, unacetalated ester, acid-acetal, and other acidic material. The extracted material is then thoroughly washed to remove all residual alkali. Equivalent methods of recovery would be obvious to the skilled artisan.

The next step in the preparation of the instant plasticizer is the synthesis of the acyloxy esters. If the crude BHMOA is employed as the starting material for this step, it is preferably esterified with the appropriate alkyl alcohol under acid conditions as discussed above. The esters which have been found to be useful as plasticizers in accordance with the invention include $C_1$–$C_8$ straight or branched alkyl esters. Of particular interest are the methyl, ethyl, 1-butyl, and 2-ethylhexyl esters.

The BHMOA ester is then acylated with a suitable agent (Example 10). Without desiring to be limited thereto, acyl anhydrides of the formula $(R^2CO)_2O$ and acyl halides of the formula

where $R^2$ is a $C_1$–$C_4$ straight or branched alkyl or halogen-substituted alkyl and X is a halogen have been found to be particularly useful. Exemplary of a halogen-substituted acyl anhydride is trichloroacetic anhydride. For purposes of availability, acetic anhydride and acetyl chloride are the preferred acylating agents. The reaction is catalyzed with acid, such as concentrated sulfuric, and proceeds exothermically. The acyloxy ester is then recovered by any conventional means such as vacuum distillation. The following reaction sequence describes this procedure.

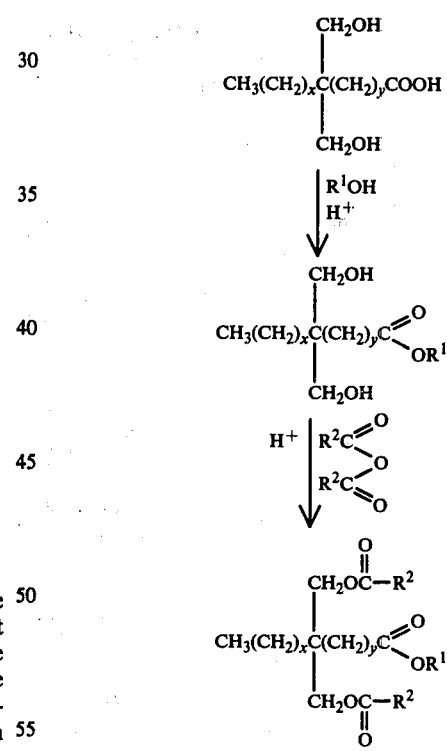

where $R^1$, $R^2$, x, and y have the same values described above in the Summary of the Invention.

The inventors have unexpectedly discovered that when the BHMOA has been purified by distillation of its acetal-ester as described above, that the acyl derivatives can be prepared directly from the acetals by reaction with the appropriate acylating agents (Example 11). For example, the BHMOA acetone acetal methyl ester prepared above can be converted to its acyloxymethyl counterpart as follows:

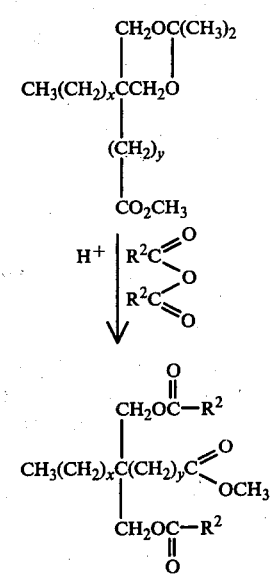

where $R^2$, $x$, and $y$ have the same values described above in the Summary of the Invention.

If necessary, a different ester group can be substituted for that which was employed in the purification step. The conversion is best effected prior to acylation in order to avoid partial deacylation. In the preferred procedure, the acetal ester is saponified with aqueous base to the acid acetal. The acid acetal is then esterified with the appropriate alcohol in the presence of acid catalyst. Alternatively, the acetal ester can be transesterified in a one-step reaction in the presence of the appropriate alcohol and a nonaqueous base as well known in the art. Suitable nonaqueous bases include sodium methoxide, sodium ethoxide, and sodium t-butoxide. It is noted that in any of the above-described esterifications, self-esterification of the BHMOA may occur. Such material constitutes the pot residue upon distillation and can be saponified with base to the BHMOA for use in recycling.

The thus prepared esters of 9,9(10,10)-bis(acyloxymethyloctadecanoic acid have surprisingly long liquid ranges, from less than $-70°$ C. to at least about 200° C. at 0.005 mm. of Hg. They are also remarkably stable, with no indication of decomposition on repeated distillation, as might be expected because of the presence of the long side chains. Their overall properties as plasticizers for PVC are unexpectedly superior to the prior art plasticizers discussed above. The instant esters are compatible with any of the commercially available PVC products which normally have a molecular weight of from 50,000 to 120,000 and also with the various additives which are often included in the plastic formulation. These additives include heat stabilizers such as mixtures of metallic salts based on Pd, Ba, and Cd, and epoxidized oils; fillers and extenders which are usually relatively inexpensive high boiling compositions used to plasticize and extend the volume of the plastic, lubricants, and pigments. Those skilled in the art will know which and how much of the many available additives will be useful in combination with the instant plasticizers to give PVC products having the desired properties.

The instant plasticizers are incorporated in the mixture in plasticizing amounts from about 5 to 35% by weight and preferably in amounts from about 30 to 32% by weight. At lower concentrations the plasticized product is more rigid, having a higher tensile strength but lower flexibility. At concentrations of below 5% the plasticizer compositions act as processing aids without significantly affecting the properties of the product.

The plasticizers of the invention are not volatilized at fusion temperatures (i.e., about 160° C. for PVC) and therefore remain in the final product.

Fusion of PVC and plasticizer is normally accomplished by combining all the desired ingredients and subjecting the mixture to vigorous mixing at the fusion point temperature. This is preferably done by milling the mixture in a rubber mill, such as a Banbury mixer, at about 160° C. for about 8 min. The fused composition is then transferred to a suitable heat mold which is maintained at 160° C. for about 10 min., then a pressure of about 1,000 p.s.i.g. is applied for about 10 min. while the 160° C. temperature is maintained. The mold is usually cooled to room temperature under pressure.

The following examples are intended only to further illustrate the invention and are not intended to limit the scope of the invention which is defind by the claims.

EXAMPLE 1

Preparation of 9,9(10,10)-bis(hydroxymethyl)octadecanoic acid (BHMOA) from FSA in methanol. An unstoppered 5,000-ml. 3-necked flask with a thermometer inserted through one neck was placed in an ice bath on a magnetic stirrer. A solution of 120 g. (3 moles) sodium hydroxide in 500 ml. water was stirred and cooled to about 2° C. Formaldehyde solution (225 g., 37.4%; 84.2 g., 2.8 moles formaldehyde) was added by means of an addition funnel. Addition was regulated to maintain a temperature less than 10° C. and required 37 min. A solution of 477 g. FSA (72.0%; 343 g., 1.1 moles) in methanol (total volume 1,800 ml.) was then added in the same manner over 2 hr. and 55 min. The ice bath was removed after addition and the reaction mixture stirred overnight at room temperature. The mixture was then chilled to about 10° C. and filtered to remove insoluble sodium stearate. The filter cake was washed with methanol and air dried (41.6 g.). The filtrate was concentrated to about 1,500 ml. on the rotary evaporator, diluted with 500 ml. water, acidified with 500 ml. 25% sulfuric acid, and extracted with 2 × 1,000 ml. diethyl ether. The combined ether extracts were washed with 4 × 500 ml. water, filtered, and dried over magnesium sulfate. After drying, the solution was filtered and the filtrate stripped on the rotary evaporator to leave 441 g. of viscous liquid containing 79.9% BHMOA by gas-liquid chromatography (GLC).

EXAMPLE 2

Preparation of BHMOA from FSA in water. The same procedure was followed as in Example 1 except that 100 g. FSA (92.3%; 92.3 g., 0.3 mole) was dissolved in 400 ml. water containing 14 g. (0.35 mole) sodium hydroxide. After addition, it was necessary to add 100 ml. water to the reaction mixture to facilitate stirring. The product weighed 104 g. and contained 95.9% BHMOA.

EXAMPLE 3

Preparation of BHMOA from methyl formylstearate (MFS) in methanol. The procedure of Example 1 was followed for a solution of 198 g. MFS (97.6%; 193 g., 0.59 mole) in methanol (total volume 1,000 ml.). This gave 202 g. of product, 98.3% BHMOA.

EXAMPLE 4

Preparation of methyl ester of BHMOA. A mixture of 141 g. BHMOA (98%; 138 g., 0.4 mole), 500 ml. methanol, and 1 ml. concentrated sulfuric acid was heated to reflux. A sample taken after 1 hr. showed that esterification was complete. The reaction mixture was cooled, 9 ml. of 10% sodium hydroxide solution was added, and the solution stripped on the rotary evaporator. The residue was dissolved in 500 ml. ether, washed with 4 × 250 ml. water, filtered, and dried over magnesium sulfate. Filtration and evaporation left 147 g. of liquid, 96.6% BHMOA methyl ester by GLC.

EXAMPLE 5

Preparation of BHMOA acetone acetal butyl ester. A mixture of 90 g. 9,9(10,10)-bis(hydroxymethyl)octadecanoic acid (82%; 74 g., 0.21 mole), 500 ml. 1-butanol, and 0.1 g. p-toluenesulfonic acid was refluxed for 1 hr. and then stripped on the rotary evaporator. GLC of the residue showed 90% conversion to the butyl ester. This material was dissolved in 500 ml. acetone and 100 ml. dimethoxypropane, stirred for 0.5 hr., and then let stand overnight at room temperature. Five milliliters of 10% NaOH was then added with vigorous stirring. The mixture was then stripped on the rotary evaporator. The residue was dissolved in 500 ml. petroleum ether. This solution was washed with 4 × 100 ml. water, filtered, and dried over magnesium sulfate. After removal of the drying agent and evaporation of the solvent, there remained 105 g. of product containing 80% (GLC) 1-butyl 9,9(10,10)-bis(hydroxymethyl)octadecanoate acetone acetal.

EXAMPLE 6

Preparation of BHMOA acetone acetal. A solution of 110 g. BHMOA (82%; 90.2 g., 0.26 mole), 500 ml. acetone, 50 ml. dimethoxypropane (DMP), and 0.1 g. p-toluenesulfonic acid was stirred at room temperature for 0.5 hr., then let stand overnight. After addition of 2 ml. 10% sodium hydroxide solution, the mixture was stripped on the rotary evaporator. The residue was dissolved in 500 ml. of petroleum ether (boiling range 38.0°–45.9° C.), washed with 2 × 100 ml. water, filtered, and dried over magnesium sulfate. Filtration and evaporation gave 113 g. product, 78% BHMOA acetone acetal (GLC).

EXAMPLE 7

Preparation of BHMOA acetone acetal methyl ester. a) A solution of 213 g. of BHMOA acetone acetal (98.7%; 210.2 g., 0.55 mole), 300 ml. methanol, 750 ml. DMP, and 0.4 g. p-toluenesulfonic acid was stirred at room temperature overnight. Another 0.2 g. p-toluenesulfonic acid was added, the solution refluxed for 1 hr. and again stirred overnight. Solid sodium bicarbonate was added and the mixture stirred vigorously for 15 min., filtered, and stripped on the rotary evaporator. The residue was dissolved in 1,000 ml. petroleum ether, washed with 4 × 250 ml. water, filtered, and dried over magnesium sulfate. Filtration and evaporation left 216 g. of product, 94.5% BHMOA acetone acetal methyl ester by GLC. This was distilled at 187°–220° C./0.01–0.02 mm. to give 158 g. of distillate, 94.8% BHMOA acetone acetal methyl ester. There was 50 g. (23.7%) pot residue.

b) In another experiment, a solution of 215 g. of undistilled product containing 90.9% BHMOA acetone acetal methyl ester in 1,000 ml. petroleum ether was washed with 2 × 250 ml. water, 2 × 250 ml. 5% sodium hydroxide solution, 7 × 250 ml. water, 250 ml. 5% sulfuric acid, and 3 × 250 ml. water, filtered, and dried over magnesium sulfate. Filtration and evaporation left 167 g. of product containing 96.4% ester. The basic washes were acidified and extracted with ether to give 46 g. of material containing 5.9% BHMOA, 64.2% BHMOA acetone acetal, and 13.3% BHMOA acetone acetal methyl ester. Distillation of the main product at 196°–206° C./0.005 mm. gave 136 g. distillate, 99.9% BHMOA acetone acetal methyl ester. There was 26 g. (16%) pot residue.

EXAMPLE 8

One-step preparation of BHMOA acetone acetal methyl ester.

A solution of 536 g. crude BHMOA (84%; 450 g., 1.3 moles), 800 ml. methanol, 2,000 ml. dimethoxypropane, and 1 g. p-toluenesulfonic acid was stirred at room temperature for 24 hr. Another 1 g. of p-toluenesulfonic acid was added and stirring continued another 16 hr. After refluxing for 2 hr., a third gram of p-toluenesulfonic acid was added and stirring continued at room temperature. After a total of 64 hr., GLC showed that conversion was complete. Solid sodium bicarbonate was added and the mixture stirred vigorously, filtered, and stripped on the rotary evaporator. The residue was dissolved in 2,000 ml. petroleum ether and this solution washed with 2 × 250 ml. water, 2 × 250 ml. 5% sodium hydroxide, 500 ml. 4 × 250 ml. water. The washed solution was filtered and dried, first over sodium sulfate and then over magnesium sulfate. After removal of the drying agent and evaporation of the solvent, there remained 518 g. of residue containing 85% (GLC) of product. This was distilled through a 25-cm. vacuum-jacketed Vigreux column to give a total distillate weighing 400 g. containing 85% (GLC) methyl 9,9(10,10)-bis(hydroxymethyl)octadecanoate acetone acetal.

EXAMPLE 9

Preparation of BHMOA acetone acetal ethyl ester from methyl ester. Saponification of 100 g. of distilled BHMOA acetone acetal methyl ester gave 88.3 g. of BHMOA acetone acetal acid (96.3%; 86.1 g., 0.22 mole) which was dissolved in 500 ml. absolute ethanol. p-Toluenesulfonic acid (1 g.) was added and the solution refluxed for 2 hr. Solid sodium bicarbonate was added and the solution stripped on the rotary evaporator. The residue was dissolved in 500 ml. diethyl ether and the ether solution washed with 3 × 100 ml. water, 100 ml. 10% sulfuric acid, and 4 × 100 ml. water, filtered, and dried over magnesium sulfate. Filtration and evaporation left 84.4 g. product containing 69.9% BHMOA ethyl ester and 27.0% BHMOA acetone acetal ethyl ester (GLC). This product was dissolved in 500 ml. acetone containing 50 ml. DMP and 0.2 g. p-toluenesulfonic acid. The solution was stirred at room temperature for 2 hr. Solid sodium bicarbonate was added and acetone and DMP were removed by the rotary evaporator. The residue was dissolved in 500 ml. petroleum ether and the solution washed with 2 × 100 ml. water, 2 × 100 ml. 5% sodium hydroxide solution, 4 × 100 ml. water, 100 ml. 5% sulfuric acid, and 3 × 100 ml. water.

It was then filtered and dried over magnesium sulfate. Filtration and evaporation left 70.8 g. of product, 97.5% BHMOA acetone acetal ethyl ester (GLC). This was distilled at 171°-186° C./0.005 mm. to give 67.5 g. product, 99.3% (GLC). The combined basic washes were acidified with 10% sulfuric acid and extracted with ether to give 12.7 g. material containing 67.5% BHMOA acetone acetal ethyl ester and 20.3% BHMOA acetone acetal.

EXAMPLE 10

Preparation of 1-butyl 9,9(10,10)-bis(acetoxymethyl)octadecanoate from BHMOA butyl ester. A solution of 14 g. of BHMOA butyl ester (97.8% pure) in 100 ml. acetic anhydride was stirred magnetically at room temperature. One drop of concentrated sulfuric acid was added. The temperature rose to 43° C. in 2 min. Stirring was continued for 2.5 hr. Reaction mixture was stipped on the rotary evaporator and the residue dissolved in 200 ml. petroleum ether. This solution was washed with 2 × 50 ml. water, 50 ml. 10% sodium hydroxide solution, and 3 × 50 ml. water, filtered, and dried over magnesium sulfate. Filtration and evaporation left 14.7 g. liquid, 95.2% 1-butyl 9,9(10,10)-bis(acetoxymethyl)octadecanoate.

EXAMPLE 11

Preparation of 1-butyl 9,9(10,10)-bis(acetoxymethyl)octadecanoate from BHMOA acetone acetal butyl ester. The procedure of Example 10 was repeated using 30 g. BHMOA acetone acetal butyl ester (97.2%), 150 ml. acetic anhydride, and 0.7 ml. concentrated sulfuric acid. The temperature rose to 32° C. in 12 min. The product contained 87.4% of the acetoxymethyl compound and 6.2% BHMOA butyl ester. It distilled at 196°-234° C./0.002-0.003 mm. to give a dark red distillate containing 89.2% 1-butyl 9,9(10,10)-bis(acetoxyme-thyl)-octadecanoate. There was 12.4% pot residue. Redistillation gave a yellow product.

Table I below compares the PVC plasticizing properties at a 32% incorporation level of the instant compositions (Examples 12-15) to various commercial plasticizing types (Examples 17-23) and to various prior art acyloxy and acyloxymethyl stearates (Examples 24-33) which are not of the geminal configuration. For purposes of comparison, it is to be noted that an ideal plasticizer for PVC should produce the following properties: a stiffness temperature ($T_f$) below −40° C.; a compatibility number ($T_4$-$T_f$) below 30; a tensile strength above 2,800 p.s.i.; an elongation above 290%; 100% modulus below 1,200 p.s.i.; heat stability above 10 hr.; a migration loss below 3%; and volatility loss below 1%. Migration and volatility approaching zero are desirable requirements for a permanent plasticizer. It is worth noting that all known plasticizers exhibit departure from ideality in one or more of these properties, and none is ideal in every respect.

It is noted from the Table that no single prior art biodegradable stearate plasticizer combines the properties of high heat stability with low migration and volatility losses comparable to those of the instant compositions. The control having the properties most similar to the disclosed plasticizers, that is, methyl 9,10-diacetoxy stearate (Example 32), exhibits nearly twice the volatility loss. An additional advantage of the instant 9,9(10,10) geminal plasticizers is their unique and unexpected property of imparting to PVC flexibility even at the point of failure. Moreover, they are resistant to both thermal degration and oxidation by virtue of the absence of a labile hydrogen on the bis-substituted carbon. This structural feature is nonexistent in the prior art.

Table 1

Properties of Polyvinylchloride Plasticized with Alkyl 9,9(10,10)-Bis(acyloxymethyl)octadecanoates and Prior Art Plasticizers

| Ex. No. | Plasticizer (32%) | Torsional stiffness $T_f$ (°C.) | Torsional stiffness $T_4$ (°C.) | Compatibility No. (Δ) ($T_4$-$T_f$) | Performance Tensile strength (p.s.i.) | Performance Elongation (%) | Performance 100% Modulus (p.s.i.) | Performance Heat stability (hr.) | Permanence Migration loss (%) | Permanence Volatility loss (%) |
|---|---|---|---|---|---|---|---|---|---|---|
| Instant Plasticizers: | | | | | | | | | | |
| 12. | Methyl (Acetoxy) | −24 | −2 | 22 | 2760 | 335 | 1135 | 10 | 5.1 | 0.6 |
| 13. | Ethyl (Acetoxy) | −26 | −2 | 24 | 2805 | 300 | 1135 | 9 | 5.2 | 0.5 |
| 14. | 1-Butyl (Acetoxy) | −28 | −2 | 26 | 2705 | 330 | 1090 | 11 | 6.4 | 0.6 |
| 15. | 2-Ethylhexyl (Acetoxy) | −30 | 0 | 30 | 2815 | 290 | 1290 | 11 | 5.8 | 0.6 |
| Di(2-ethylhexyl) ester controls: | | | | | | | | | | |
| 16. | Phthalate (DOP)[a] | −26 | 2 | 28 | 2805 | 320 | 1170 | 9.5 | 4.3 | 1.2 |
| 17. | Phthalate (DOP) | −25 | 4 | 29 | 2835 | 290 | 1165 | 6.5 | 3.0 | 1.5 |
| 18. | Phthalate (DOP) | −29 | 1 | 30 | 2770 | 280 | 1115 | 10 | 3.9 | 1.3 |
| 19. | Sebacate (DOS)[b] | −57 | −11 | 46 | 3570 | 315 | 925 | 10 | 19.5 | 1.2 |
| 20. | Sebacate (DOS) | −57 | −7 | 50 | 2355 | 295 | 1045 | — | 19.3 | 1.6 |
| 21. | Azelate (DOZ)[c] | −56 | −12 | 44 | 2615 | 470 | 1020 | 10 | 18.7 | 1.5 |
| Polymeric control: | | | | | | | | | | |
| 22. | Plastolein 9720 | −21 | 8 | 29 | 2830 | 305 | 1345 | 7.5 | 3.9 | 0.9 |
| Phosphate control: | | | | | | | | | | |
| 23. | Tricresyl | −1 | 18 | 19 | 2950 | 205 | 1860 | 1.5 | 0.3 | 0.3 |
| Alkyl (acyloxymethyl) stearate controls[d]: | | | | | | | | | | |
| 24. | Methyl 9(10)-(CH$_2$OCOMe) | −47 | −12 | 35 | 2725 | 380 | 905 | 12 | 15.5 | 2.3 |
| 25. | Ethyl 9(10)-(CH$_2$OAc) | −49 | −12 | 37 | 2700 | 360 | 920 | 12 | 16.7 | 2.2 |
| 26. | n-Butyl 9(10)-CH$_2$Ac) | −51 | −6 | 45 | 2680 | 325 | 1070 | 8.0 | 17.6 | 1.3 |
| 27. | 2-Ethyl-1-hexyl 9(10)-(CH$_2$Ac) | −55 | 8 | 63 | 2590 | 260 | 1195 | 8.5 | 18.5 | 2.5 |
| 28. | Methyl (CH$_2$OAc)$_2$ | −33 | −8 | 25 | 2610 | 335 | 835 | 7.0 | 8.1 | 0.8 |
| 29. | Butyl (CH$_2$OAc)$_2$ | −33 | −7 | 26 | 2820 | 345 | 935 | 9.5 | 8.0 | 0.5 |
| Alkyl (acetoxy) stearate controls[d]: | | | | | | | | | | |
| 30. | Methyl 9(10)-acetoxy | −46 | −11 | 35 | 2795 | 370 | 980 | 9.5 | 16.0 | 3.6 |
| 31. | Butyl 9(10)-acetoxy | −50 | −8 | 42 | 2620 | 270 | 1020 | 11 | 17.0 | 1.5 |
| 32. | Methyl 9,10-diacetoxy | −25 | −1 | 24 | 2840 | 335 | 975 | 11.5 | 4.5 | 1.1 |
| 33. | Butyl 9,10-diacetoxy | −33 | 2 | 35 | 2785 | 450 | 1295 | 14 | 8.0 | 1.7 |

[a]Di-2-ethylhexyl phthalate.
[b]Dioctyl sebacate.
[c]Dioctyl azelate.
[d]Reported in Frankel et al., J. Amer. Oil Chem. Soc. 52(12):498-504 (1975).

One basic requirement for a plasticizer is that all intermolecular forces be of the same order of magnitude between plasticizer and plasticizer, between polymer and polymer, and between plasticizer and polymer. To be an efficient plasticizer, a low molecular weight compound must have sufficient affinity for the polymer to overcome polymer-polymer interactions. To impart good low temperature flexibility, the compound also must retain enough mobility to participate in the equilibria of the plasticized system, and must be able to diffuse through the system. PVC, containing polar groups, requires polar plasticizers to achieve good compatibility, which depends on the proper kind, number, and arrangement of polar groups in the plasticizer. Ester groups are notable effective polar functions in plasticizers producing compatibility with PVC.

While not desiring to be bound to any particular theory, it is believed that the unexpected PVC plasticizing superiority of the instant novel compounds is attributed primarily to the sufficiently high polarity imparted by the pair of acyloxymethyl groups which mask the polar sites in the PVC polymer chain and reduce attraction forces between polymer molecules, giving them freedom of movement as required for desirable flexibility.

It is to be understood that the foregoing detailed description is given merely by way of illustration and that modification and variations may be made therein without departing from the spirit and scope of the invention.

We claim:

1. A method of preparing a plasticized polyvinylchloride composition comprising the following steps:
   a. providing a primary plasticizer compound having the following general structure:

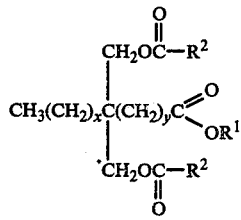

where
$R^1 = C_1-C_8$ straight or branched alkyl;
$R^2 = C_1-C_4$ straight or branched alkyl or halogen-substituted alkyl;
$x = 7$ or 8; and
$y = 7$ or 8 with the proviso that
$x + y = 15$; and
   b. fusing a plasticizing amount of the compound described in step (a) with polyvinylchloride.

2. The method of preparing a plasticized polyvinylchloride composition as described in claim 1 wherein $R^1$ is selected from the group consisting of —CH$_3$, —CH$_2$CH$_3$, —CH$_2$CH$_2$CH$_2$CH$_3$, and

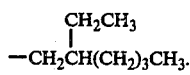

3. The method of preparing a plasticized polyvinylchloride composition as described in claim 2 wherein $R^2$ is selected from the group consisting of —CH$_3$ and —CCl$_3$.

4. The method of preparing a plasticized polyvinylchloride composition as described in claim 2 wherein $R^2$ is —CH$_3$.

5. The method of preparing a plasticized polyvinylchloride composition as described in claim 1 wherein $R^1$ and $R^2$ are —CH$_3$.

6. In a plasticized polyvinylchloride composition an improvement comprising a plasticizing amount of a primary plasticizer wherein said plasticizer is a compound having the general structure:

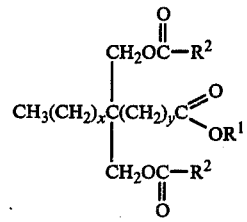

where
$R^1 = C_1-C_8$ straight or branched alkyl;
$R^2 = C_1-C_4$ straight or branched alkyl or halogen-substituted alkyl;
$x = 7$ or 8; and
$y = 7$ or 8 with the proviso that
$x + y = 15$.

7. A plasticized polyvinylchloride composition as described in claim 6 wherein the primary plasticizer is present in an amount equaling from 5 to 35% of the total weight of the composition.

8. A plasticized polyvinylchloride composition as described in claim 6 where $R^1$ is selected from the group consisting of —CH$_3$, —CH$_2$CH$_3$, —CH$_2$CH$_2$CH$_2$CH$_3$, and

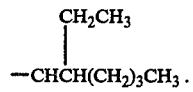

9. A plasticized polyvinylchloride composition as described in claim 6 wherein $R^2$ is selected from the group consisting of —CH$_3$ and —CCl$_3$.

10. A plasticized polyvinylchloride composition as described in claim 8 wherein $R^2$ is —CH$_3$.

11. A plasticized polyvinylchloride composition as described in claim 6 wherein $R^1$ and $R^2$ are —CH$_3$.

12. The novel compounds having the general structure:

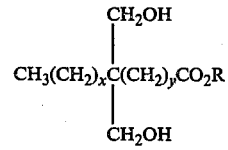

where
R = H or $C_1-C_8$ straight or branched alkyl;
$x = 7$ or 8; and
$y = 7$ or 8 with the proviso that $x + y = 15$.

13. A novel compound as described in claim 12 wherein R = H.

* * * * *